US008889421B1

(12) United States Patent
Ouellette et al.

(10) Patent No.: US 8,889,421 B1
(45) Date of Patent: Nov. 18, 2014

(54) BULK HME PRECURSOR DETECTION KIT (75) Inventors: Wayne Ouellette, Waldorf, MD (US);
John H. Wilkinson, Waldorf, MD (US);
James N. Thomasson, III, Alexandria, VA (US); Frederick S. Heim, Pearisburg, VA (US); Herbert Mitchell, Severna Park, MD (US); Robert G. Best, Burke, VA (US)

(73) Assignee: The United States of America as Represented by the Secretary of the Navy, Washington, DC (US)

( * ) Notice: Subject to any disclaimer, the term of this patent is extended or adjusted under 35 U.S.C. 154(b) by 585 days.

(21) Appl. No.: 13/137,521

(22) Filed: Aug. 24, 2011

(51) Int. Cl.
*G01N 31/22* (2006.01)
*G01N 33/52* (2006.01)

(52) U.S. Cl.
USPC .......... 436/110; 422/430; 436/100; 436/101; 436/106; 436/107; 436/108; 436/124; 436/166

(58) Field of Classification Search
USPC .......... 422/430; 436/100–101, 106–108, 110, 436/124, 166
See application file for complete search history.

(56) References Cited

U.S. PATENT DOCUMENTS

| | | | | | |
|---|---|---|---|---|---|
| 3,446,599 | A | * | 5/1969 | Shand | 436/97 |
| 3,531,254 | A | * | 9/1970 | Okuda | 436/108 |
| 3,802,842 | A | * | 4/1974 | Lange et al. | 436/169 |
| 3,817,705 | A | * | 6/1974 | Schmitt et al. | 436/110 |
| 3,826,620 | A | * | 7/1974 | Davis et al. | 422/420 |
| 4,595,430 | A | * | 6/1986 | Baker | 149/88 |
| 4,690,902 | A | * | 9/1987 | Bitsch | 436/110 |
| 4,788,039 | A | * | 11/1988 | Glattstein | 422/430 |
| 4,904,605 | A | * | 2/1990 | O'Brien et al. | 436/169 |
| 4,938,926 | A | * | 7/1990 | Reiss | 422/417 |
| 5,100,621 | A | * | 3/1992 | Berke et al. | 422/430 |
| 5,296,380 | A | * | 3/1994 | Margalit | 436/106 |
| 5,480,612 | A | * | 1/1996 | Margalit | 422/430 |
| 5,648,047 | A | * | 7/1997 | Kardish et al. | 422/411 |
| 6,613,576 | B1 | * | 9/2003 | Rodacy et al. | 436/164 |
| 7,410,612 | B1 | * | 8/2008 | Carrington | 422/531 |
| 7,829,020 | B2 | * | 11/2010 | Pagoria et al. | 422/402 |
| 7,846,740 | B2 | | 12/2010 | Amisar | |
| 8,377,713 | B2 | * | 2/2013 | Miller et al. | 436/172 |
| 2005/0287036 | A1 | * | 12/2005 | Eckels et al. | 422/61 |
| 2006/0084176 | A1 | * | 4/2006 | Almog | 436/110 |
| 2009/0029480 | A1 | | 1/2009 | Loane | |
| 2010/0000882 | A1 | | 1/2010 | Wang et al. | |
| 2012/0003746 | A1 | * | 1/2012 | Amisar | 436/110 |

FOREIGN PATENT DOCUMENTS

WO    WO 79/00122    *  3/1979

OTHER PUBLICATIONS

Chrostowski, J. E. et al, Arson Analysis News 1981, 5, 14-18.*
Synthesis procedure for azocoupling benzene diazoniuim chloride with 2 naphthol to form 1-phenylazo-2-naphthol Mar. 2006, 6 pages, downloaded from http://www.oc-praktikum.de/nop/en/instructions/pdf/1017_en.pdf.*

(Continued)

*Primary Examiner* — Arlen Soderquist
(74) *Attorney, Agent, or Firm* — Fredric J. Zimmerman (57) ABSTRACT

The present invention relates generally to a kit and method for the colorimetric detection of precursors used in the assembly of homemade explosives (HMEs). More specifically, the present invention relates to a bulk HME precursor detection kit and methods of using a kit that is capable of bulk detection of HME precursors, such as urea nitrate, ammonium nitrate and potassium chlorate.

12 Claims, 5 Drawing Sheets

(56) References Cited

OTHER PUBLICATIONS

Booklet titled "Identifying Unknown Chemicals in Science Labs" Sep. 2009, 6 pages, published by the Florida Department of Environmental Protection.*

* cited by examiner

BULK HME PRECURSOR DETECTION KIT

STATEMENT OF GOVERNMENT INTEREST

The invention described herein may be manufactured and used by or for the Government of the United States of America for governmental purposes without the payment of any royalties thereon or therefore.

FIELD OF INVENTION

The present invention relates generally to a kit and method for the colorimetric detection of precursors used in the assembly of homemade explosives (HMEs). More specifically, the present invention relates to a bulk HME precursor detection kit and methods of using a kit that is capable of bulk detection of HME precursors, such as urea nitrate, ammonium nitrate and potassium chlorate.

BACKGROUND OF THE INVENTION

The detection of explosives is an important component of modern warfare, and devices capable of detecting explosive residues are of great importance. In particular, homemade explosives (HMEs) are frequently found in the theatre of war, as HMEs are prepared from components that are easily synthesized from readily available precursor chemicals.

Currently, there are several commercial test kits that have the ability to detect the presence of some precursors commonly used for making HMEs. However, these kits are typically not specifically designed for soldiers performing tactical operations. In particular, most commercial test kits are typically too large, heavy and cumbersome to be practical for tactical operations. Furthermore, soldiers performing tactical operations typically come in contact with bulk quantities of HME precursors. However, the majority of all existing commercial test kits focus solely on trace detection and are not optimized for bulk detection, and hence do not provide a tactical advantage to a soldier in the theater of war. Additionally, most commercial colorimetric test kits are designed to detect most HME precursors, HMEs and military grade explosives all in one test kit. This comprehensive testing approach unfortunately leads to confusion for the end user, an unacceptable level of false positives and negatives, and a decrease in the overall effectiveness of the test kit.

Accordingly, there is a need for an effective bulk HME precursor detection kit that is portable, lightweight, easy to use, low cost, provides focused detection and provides true bulk detection. Further, it would be highly advantageous if the bulk HME precursor detection kit were designed to focus only on detecting primary threat materials found in a specific conflict or theater of operations, thereby reducing confusion for the end user and increasing detection effectiveness and reliability.

SUMMARY OF THE INVENTION

The present invention relates generally to a kit and method for the colorimetric detection of precursors used in the assembly of homemade explosives (HMEs). More specifically, the present invention relates to a bulk HME precursor detection kit and methods of using a kit that is capable of bulk detection of HME precursors, such as urea nitrate, ammonium nitrate and potassium chlorate.

Exemplary embodiments of the invention relate to a detection kit for detecting the presence of a bulk homemade explosive (HME) precursor in a sample comprising: at least one vial for holding a dry sample of the HME precursor; at least one nitrate test strip for detecting the presence of nitrates in the sample; at least one reagent for detecting the presence of ureas in the sample; and at least one potassium iodide/starch test strip for detecting the presence of chlorates in the sample.

Additionally, in various embodiments of the detection kit, the nitrate test strip turns purple when nitrate is present in the sample. In further exemplary embodiments, at least one reagent is Ehrlich's reagent. In even further embodiments, the potassium iodide/starch test strip turns blue or black when chlorate is present in the sample. Other aspects of the invention may also feature a detection kit where the nitrate test strip further comprises nitrate reductase. In another aspect of the detection kit, the nitrate test strip further comprises sulfanilamide and N-(1-naphthyl)-ethylene diamine. Other embodiments of the detection kit may also include HCl solution as a reagent.

Other exemplary embodiments of the invention relate to a method of detecting the presence of a bulk HME precursor using a detection kit, including the steps of providing a dry sample suspected of containing bulk HME precursors; mixing the sample with an aqueous solution in a vial; inserting a nitrate test strip to detect for the presence of nitrates in the sample; adding a reagent to the vial to detect for the presence of ureas in the sample; and inserting a potassium iodide/starch test strip to detect for the presence of chlorates in the sample, where the step of inserting the potassium iodide/starch test strip is performed only when the prior steps produce negative results for the presence of nitrates and ureas.

DETAILED DESCRIPTION OF THE INVENTION

The present invention relates generally to a kit for the colorimetric detection of precursors used in the assembly of homemade explosives (HMEs). More specifically, the present invention relates to a bulk HME precursor detection kit (hereinafter "detection kit") that is capable of bulk detection of HME precursors, such as urea nitrate, ammonium nitrate and potassium chlorate. The present invention also provides a method of using the detection kit to detect HME precursors.

When the terms "one," "a," or "an" are used in this disclosure, they mean "at least one" or "one or more," unless otherwise indicated.

In accordance with the present invention, an exemplary detection kit capable of detecting various bulk HME precursors, such as urea nitrate, ammonium nitrate and potassium chlorate, is shown in FIG. 1. The detection kit may be implemented in various configurations, and is not limited to the particular exemplary detection kits disclosed herein. The invention covers all modifications, equivalents, and alternatives falling within the spirit and scope of the invention as defined by the claims.

The present invention is a detection kit and method of using a detection kit that is capable of detecting bulk HME precursors. Examples of HME precursors include nitrate based oxidizers, such as ammonium nitrate and potassium nitrate. Additional examples of HME precursors include urea and urea nitrate, and potassium chlorate.

Nitrate Based Oxidizers

Nitrate based oxidizers represent one type of HME precursor. In an exemplary embodiment, the detection of nitrate based oxidizers may be conducted according to the following chemical reaction scheme:

Step 1.

Nitrate ($NO_3^-$)+Nitrate reductase→Nitrite ($NO_2^-$)

Step 2.

NED=N-(1-naphthyl)-ethylene diamine

In step 1 of the above exemplary embodiment, nitrate ions are reduced to nitrite ions with the addition of the enzyme nitrate reductase. The addition of nitrate reductase can be achieved by using nitrate anion detection strips (for example, sold by EMD Chemicals, Inc., Gibbstown, N.J.) or any equivalent commercially available detection strip containing the nitrate reductase.

In step 2, nitrite ions react with the aromatic amine, sulfanilamide, in the presence of an acidic buffer to form a diazonium salt. The diazonium salt then reacts with NED to form a red/violet azo dye.

Urea/Urea Nitrate

Another HME precursor is urea or urea nitrate (hereinafter "ureas"). In an exemplary embodiment of the present invention, the detection kit may be equipped with Ehrlich's reagent to detect the presence of urea or urea salts such as urea nitrate. Ehrlich's reagent is a well-established and characterized reagent that reacts chromatometrically with ureas, and has been used extensively in the determination of ureas in biological fluids, urethane resins, soil, water and feed stocks.

Ehrlich's reagent is composed of 2% 4-(dimethylamino) benzaldehyde and 20% HCl in alcohol (methanol, ethanol, propanols, butanol, pentanol). The reaction of urea or uronium cations with 4-(dimethylamino)benzaldehyde results in (E)-1-(4-(dimethylamino)benzilidene)uronium chloride, which produces a yellow to yellow green color. The yellow color produced by the product of the reaction is due to simple Schiff bases with quinoid resonating structures. An exemplary chemical reaction scheme is as follows:

Schiff base with quinoid resonating structure resulting in yellow color.

Potential pitfalls of this method include the suppression of color development due to dilution, as expected for a reversible reaction of this type, and decrease in color relative to hydrochloric acid concentrations either above or below optimal level. Optimal concentrations, solvents and conditions of the Ehrlich's reagent to avoid these pitfalls can easily be ascertained with routine optimization experiments.

Potassium Chlorate

Another HME precursor that may be detected using a detection kit as described is potassium chlorate. The detection of potassium chlorate relies upon the liberation of $I_2$ in solution, which produces an immediate color change to dark red/violet in the presence of chlorate anions. In an exemplary embodiment, the detection of potassium chlorate may be conducted according to the following chemical reaction scheme:

$ClO_3^- + 6I^- + 6H^+ \rightarrow Cl^- + 3I_2 + 3H_2O$ $KClO_3 + 6KI + 6HCl \rightarrow 3H_2O + 7KCl + 3I_2$ (dark red/violet) (blue/black in presence of starch)

In the chemical reaction scheme shown above, the liberation of $I_2$ produces a deep dark color, which is immediate and easily seen. Furthermore, when starch is added, the color is intense blue/black when $I_2$ is liberated. Accordingly, the detection of $I_2$ may be achieved by using potassium iodide/starch test strips (for example, sold by Fisher Scientific, Pittsburgh, P.A.) or any equivalent commercially available detection strip.

In various exemplary detection kits, the test for potassium chlorate may be optimized for the detection of bulk quantities of chlorates and chlorate mixtures with sugar and aluminum. Liquid calcium hypochlorite and household liquid bleach will produce a false positive. Liquid peroxides will immediately produce a black color in these test strips. However, the scope of this test kit is for bulk powders or "prills" found in theater and is not intended for use on liquid samples. The dilute HCl solution required for this test will not ignite potassium chlorate/sugar mixtures and will not result in severe burns to the skin (mild irritation). This chemistry is available in the form of a test strip. Potassium iodide/starch test strips are available from Fisher Scientific.

Detection Kit

Figure 1A:
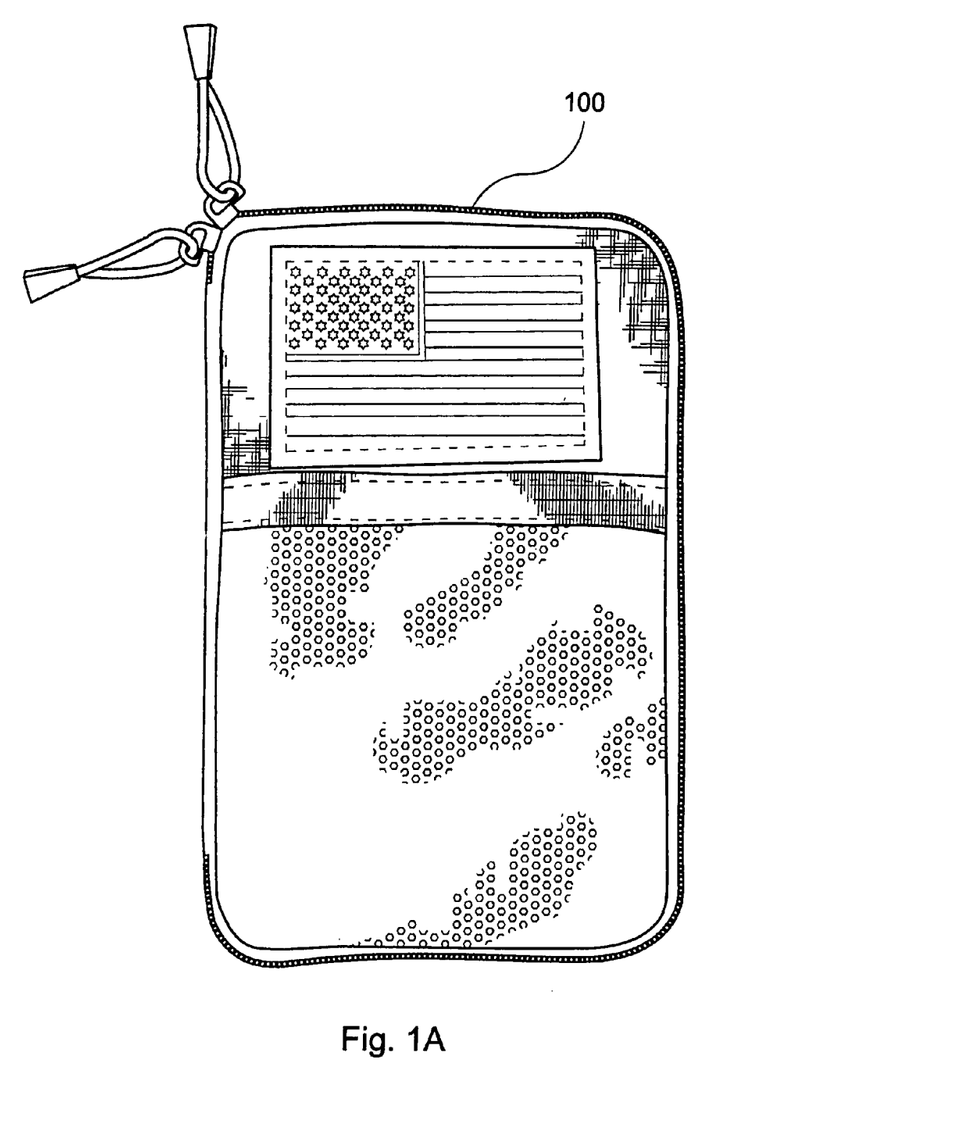
FIG. 1A shows an exemplary bulk HME precursor detection kit.

Referring to the drawings for the purpose of describing exemplary embodiments of the present invention, FIG. 1A shows a bulk HME precursor detection kit. As discussed, the detection kit may be designed and modified to identify various levels of bulk quantities of ureas, nitrates, and/or chlorates.

Figure 1B:
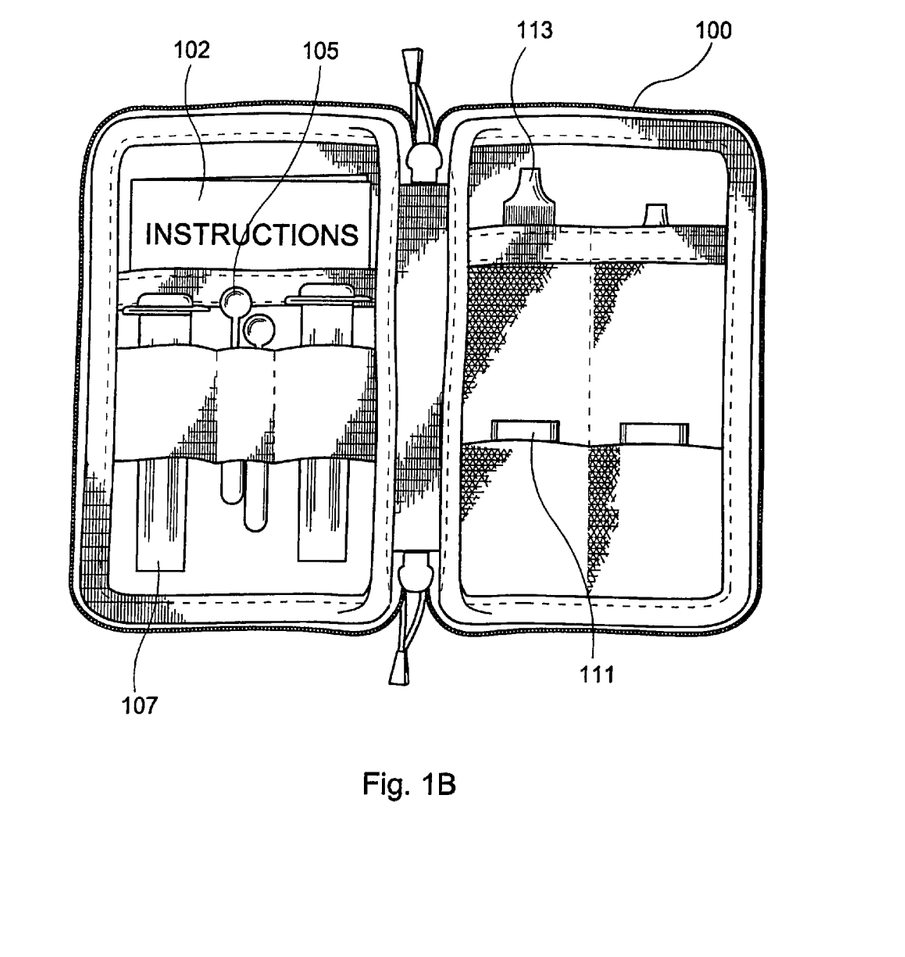
FIG. 1B shows an interior view of an exemplary bulk HME precursor detection kit.
Figure 1C:
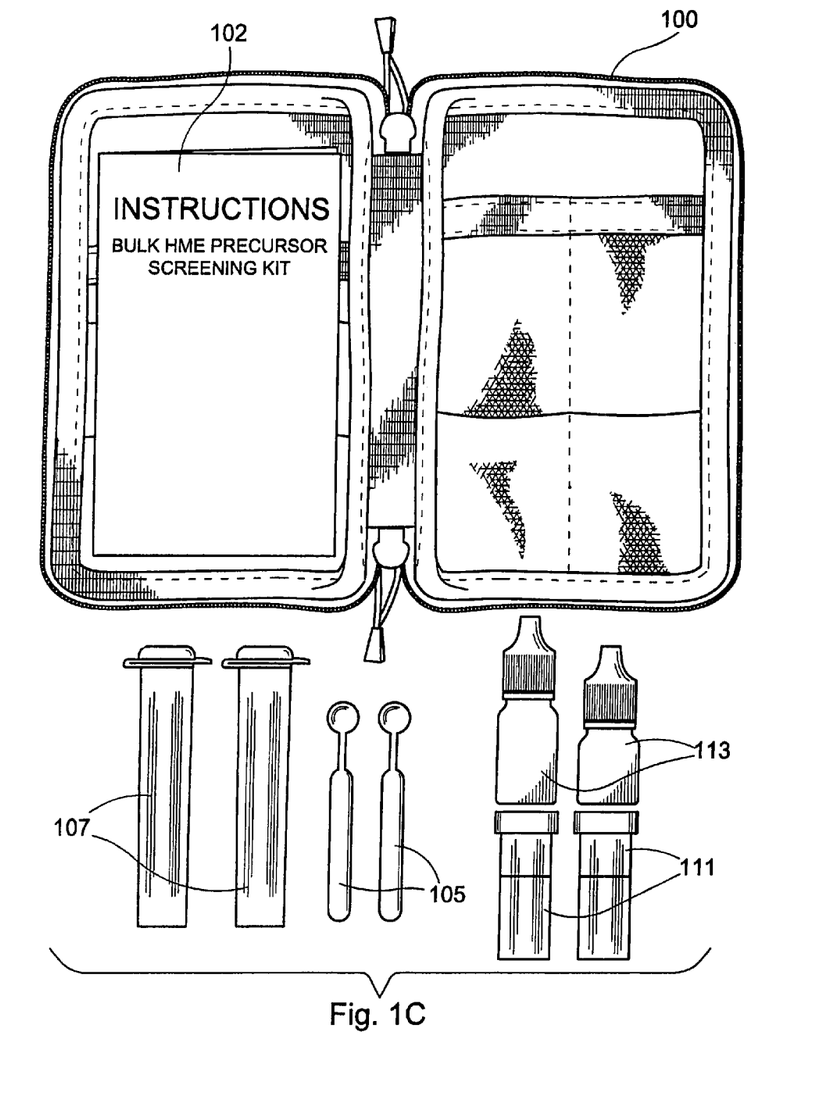
FIG. 1C shows another interior view of an exemplary bulk HME precursor detection kit wherein the kit components are shown.
Figure 1D:
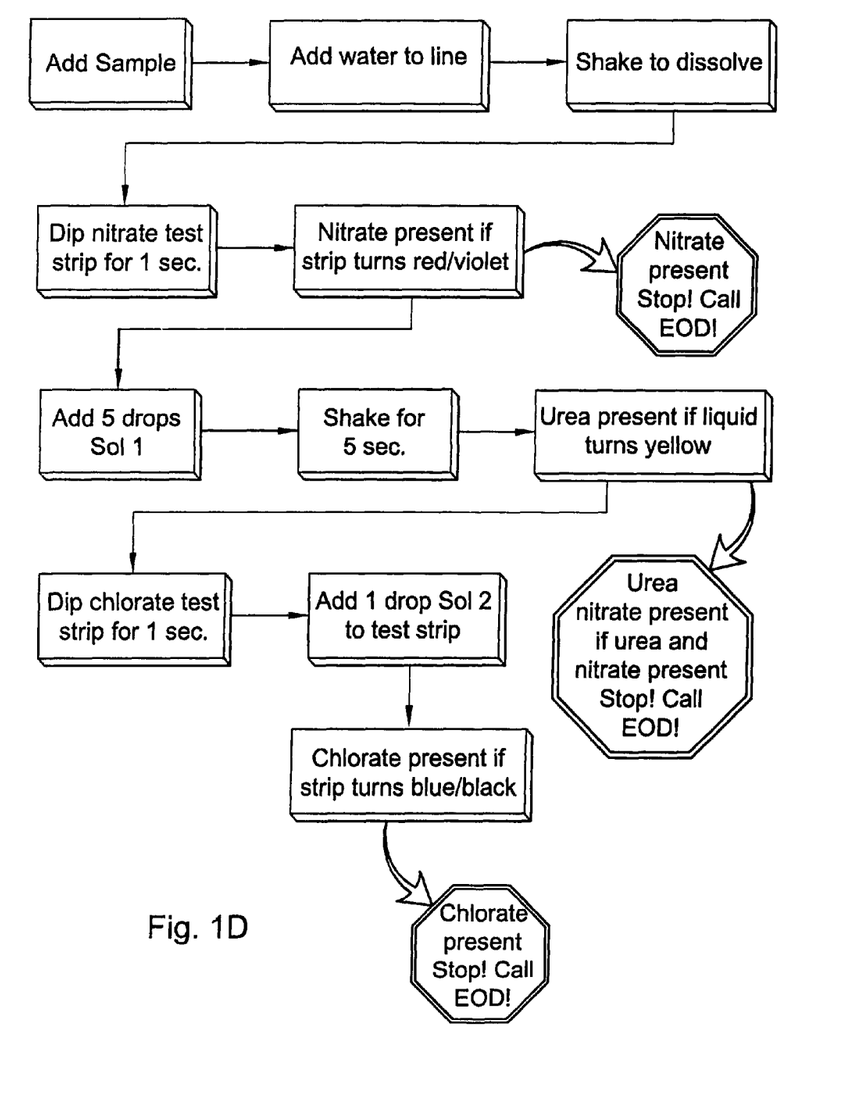
FIG. 1D is a flow diagram illustrating an exemplary embodiment of a method of using a bulk HME precursor detection kit.

As shown in FIGS. 1A, 1B and FIG. 1C, the detection kit includes a pocket pouch 100, an instruction card 102, two sampling spoons 105, two test vials 111, for example, styrene test vials, two reagents 113 and two test strips 107. More particularly, in various embodiments the two reagents 113 may include a urea test reagent and HCl provided in dropper bottles. Further, the two test strips 107 may include nitrate test strips (e.g., EMD Cat#10020-1) and KI/starch test strips (e.g., Fisher Scientific Cat#14-860). Various modifications including the sample size of the sampling spoons 105, capacity of the test vials 111 and number of test strips 107 provided are contemplated within the scope of the invention. In another exemplary embodiment, the size of the pocket pouch may be modified to include extra sampling spoons, test vials, and test strips. Additionally, FIG. 1D illustrates an exemplary flow chart that may be provided on the instruction card 102 as a reference.

Methods of Using

Figure 2:
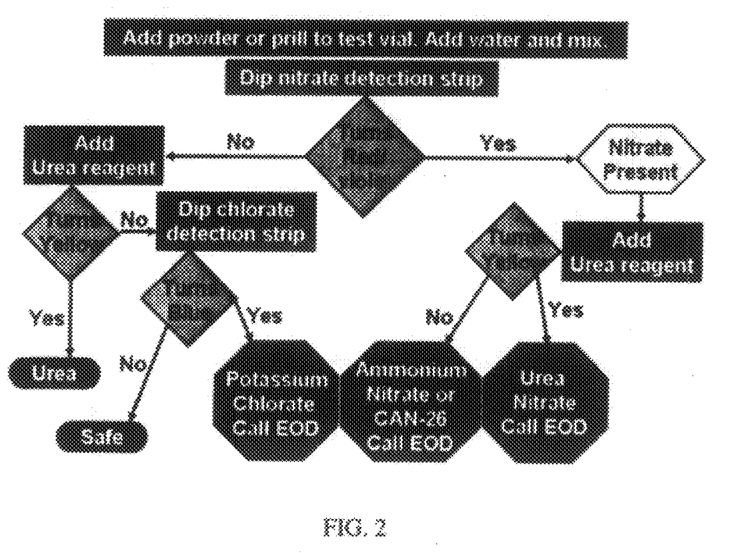
FIG. 2 is a flow diagram illustrating another exemplary embodiment of a method of using a bulk HME precursor detection kit.

In accordance with the present invention, there is provided a method of using a detection kit as described herein to detect bulk HME precursors. FIG. 2 depicts a flow chart of an exemplary embodiment of the invention. In one embodiment, the method of the present invention includes the following steps:

Step 1: Add one level spoonful of powder to vial. Fill vial to line with water, seal the vial and shake until the sample is dissolved.

Step 2: Insert a nitrate test strip into mixture for 1 second. Nitrate is present if test strip turns light red to dark purple within 5 seconds.

Step 3: Add 5 drops of urea test reagent (e.g., Ehrlich's reagent) to the vial, seal the vial and shake vigorously for 5 seconds. Uronium ions are present if the liquid turns yellow immediately after shaking. Nitrate based fertilizers are present with a positive result for nitrate and a negative result for urea. Urea is present if a positive result for uronium ions and a negative result for nitrate is obtained. Urea nitrate is present if a positive result for uronium ions and a positive result for nitrate is obtained.

Step 4: Insert a chlorate test strip (e.g., potassium iodide/starch) into mixture for 1 second. Remove the test strip and add one drop of HCl directly onto the test strip. Chlorate is present if the test strip turns blue or black within 5 seconds.

In the exemplary embodiment described above, there are five different test result scenarios for possible precursor identification, as shown in Table 1:

TABLE 1

| Nitrate | Urea | Chlorate | Material Identification |
| --- | --- | --- | --- |
| Positive | Negative | Negative | Ammonium nitrate, potassium nitrate, CAN-27 - Alert EOD |
| Negative | Positive | Negative | Urea - Legal Fertilizer |
| Positive | Positive | Negative | Urea nitrate - Alert EOD |

TABLE 1-continued

| Nitrate | Urea | Chlorate | Material Identification |
| --- | --- | --- | --- |
| Negative | Negative | Positive | Sodium chlorate or potassium chlorate - Alert EOD |
| Negative | Negative | Negative | Material does not contain nitrates, chlorates or urea. |

As illustrated in Table 1, material identification is determined based on testing for nitrates, ureas and chlorates. As depicted, when only nitrate is detected by a detection kit, the material identification indicates the presence of ammonium nitrate, potassium nitrate or calcium ammonium nitrate containing 27% nitrogen (CAN-27), and the Explosive Ordnance Disposal (EOD) should be alerted. When only uronium ions are detected, the material identification indicates the presence of urea in amounts equivalent to legal fertilizers. Additionally, when only chlorate is detected, the material identification indicates the presence of sodium chlorate or potassium chlorate, and the EOD should be alerted. Further, when none of the three precursors discussed are detected, the sample does not contain nitrates, chlorates or urea in bulk quantities.

The disclosure set forth above is provided to give those of ordinary skill in the art with a complete disclosure and description of how to make and use various embodiments of the invention, and are not intended to limit the scope of what the inventors regard as their invention. Modifications of the above-described modes (for carrying out the invention that are obvious to persons of skill in the art) are intended to be within the scope of the following claims. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention. All publications, patents, and patent applications cited in this specification are incorporated herein by reference as if each such publication, patent or patent application were specifically and individually indicated to be incorporated herein by reference.

Finally, any numerical parameters set forth in the specification and attached claims are approximations (for example, by using the term "about") that may vary depending upon the desired properties sought to be obtained by the embodiments of the present invention. At the very least, and not as an attempt to limit the application of the doctrine of equivalents to the scope of the claims, each numerical parameter should at least be construed in light of the number of significant digits and by applying ordinary rounding.

What is claimed is:

1. A detection kit for detecting the presence of a bulk homemade explosive (HME) precursor in a sample, comprising:
    at least one vial for holding a dry sample of the HME precursor;
    at least one nitrate test strip for detecting the presence of nitrates in the sample;
    at least one reagent for detecting the presence of ureas in the sample; and
    at least one potassium iodide/starch test strip for detecting the presence of chlorates in the sample.

2. The detection kit of claim 1, wherein the nitrate test strip turns purple when nitrate is present in the sample.

3. The detection kit of claim 1, wherein said at least one reagent is Ehrlich's reagent.

4. The detection kit of claim 1, wherein the potassium iodide/starch test strip turns one of blue and black when chlorate is present in the sample.

5. The detection kit of claim 1, wherein the nitrate test strip further comprises nitrate reductase.

6. The detection kit of claim 1, wherein the nitrate test strip further comprises sulfanilamide and N-(1-naphthyl)-ethylene diamine.

7. The detection kit of claim 1, wherein said at least one reagent is HCl solution.

8. A method of detecting the presence of a bulk HME precursor using a detection kit, comprising:
  providing a sample suspected of containing bulk HME precursors;
  mixing the sample with an aqueous solution in a vial;
  inserting a nitrate test strip in the sample for detecting a presence of nitrates;
  adding a reagent to the vial for detecting a presence of ureas in the sample; and
  inserting a potassium iodide/starch test strip for detecting a presence of chlorates in the sample,
  wherein said sample is a dry sample, and
  wherein the step of inserting the potassium iodide/starch test strip is performed only when negative results are produced for both the presence of nitrates and ureas.

9. The method according to claim 8, further comprising removing the potassium iodide/starch test strip, and adding an HCL solution to the potassium iodide/starch test strip.

10. A detection kit for detecting a presence of a bulk homemade explosive (HME) precursor in a sample, comprising:
  at least one vial for holding a dry sample of the HME precursor;
  at least one color changing test strip for detecting a presence of the HME precursor in the sample; and
  an Ehrlich's reagent for placement in said at least one vial for detecting the HME precursor,
  wherein the HME precursor is ureas.

11. A method of detecting the presence of a bulk HME precursor using a detection kit, comprising:
  providing a sample suspected of containing the bulk HME precursor;
  mixing the sample with an aqueous solution in a vial;
  inserting at least one color changing test strip in the sample for detecting a presence of the HME precursor; and
  observing a color change to the said at least one color changing test strip.

12. The method of detecting the presence of a bulk HME precursor using a detection kit according to claim 11, wherein the HME precursor is nitrates.

* * * * *